(12) United States Patent
Muessig et al.

(10) Patent No.: US 7,693,575 B2
(45) Date of Patent: Apr. 6, 2010

(54) HEART STIMULATOR WITH OVERRIDE FOR STIMULATION EXCEEDING A MAXIMUM RATE

(75) Inventors: Dirk Muessig, West Linn, OR (US); Kurt Swenson, Dayton, OR (US)

(73) Assignee: Biotronik CRM Patent AG (CH)

( * ) Notice: Subject to any disclaimer, the term of this patent is extended or adjusted under 35 U.S.C. 154(b) by 319 days.

(21) Appl. No.: 11/563,279

(22) Filed: Nov. 27, 2006

(65) Prior Publication Data
US 2008/0125823 A1    May 29, 2008

(51) Int. Cl.
*A61N 1/362* (2006.01)
(52) U.S. Cl. .............................. 607/9; 607/14; 607/15; 607/27; 607/28
(58) Field of Classification Search .............. 607/9, 607/17, 28, 4, 14, 15, 18, 19, 25, 27
See application file for complete search history.

(56) References Cited

U.S. PATENT DOCUMENTS 4,875,483 A * 10/1989 Vollmann et al. ............. 607/15
6,122,546 A * 9/2000 Sholder et al. ................. 607/9

* cited by examiner

*Primary Examiner*—Carl H Layno
*Assistant Examiner*—Pamela M Bays
(74) *Attorney, Agent, or Firm*—Craig A. Fieschko, Esq.; DeWitt Ross & Stevens S.C.

(57) ABSTRACT

A heart stimulator for electrical stimulation of a heart chamber includes a sensing stage sensing excitation of the heart chamber via an electrode lead having an electrode for picking up heart chamber electric potentials, a stimulation pulse generator generating electric stimulation pulses for delivery to the heart chamber via a stimulation electrode, and a control unit connected to the sensing stage and the stimulation pulse generator and being adapted to trigger the stimulation pulses at a controlled stimulation rate. A monitoring stage is provided for preventing too high of a stimulation rate for too long of a period of time, with the monitoring stage being connected to the control unit and being adapted to monitor the controlled stimulation rate, and to override the controlled stimulation rate by a fixed stimulation rate for a predetermined period of time if the average controlled stimulation rate exceeds a predetermined maximum rate.

15 Claims, 2 Drawing Sheets

HEART STIMULATOR WITH OVERRIDE FOR STIMULATION EXCEEDING A MAXIMUM RATE

FIELD OF INVENTION

This invention relates generally to the design of heart stimulators for delivering electrical stimulation pulses to one or more chamber of a heart for therapy purposes. The invention relates more particularly to implantable heart stimulators like cardiac pacemakers and/or implantable cardioverter/defibrillator providing means for inhibiting too high a stimulation rate for too long a period of time.

BACKGROUND OF THE INVENTION

Cardiac pacemakers are medical devices, usually implantable, that can be connected to or that are permanently connected to electrode leads for delivery of electrical stimulations pulses to the tissue (myocardium) of a human heart. Dual chamber pacemakers are capable of generating stimulation pulses for the atrium and the ventricle of a human heart. Biventricular pacemakers usually are capable to stimulate at least three chambers of a human heart that is the right atrium, the right ventricle and the left ventricle.

In a dual chamber pacemaker, this is realized by placing electrodes in both the right atrium and right ventricle of the heart.

Separate stimulation pulse generators are usually provided for each heart chamber (atrium or ventricle) to be stimulated.

A control unit is triggering the generation of a respective atrial or ventricular stimulation pulse according to a preprogrammed, variable timing regime in order to provide for adequate timing of the stimulation pulses. The stimulation pulses triggered by the control unit are triggered with a controlled stimulation rate controlled by the control unit. The controlled stimulation rate may depend on the physical or mental load of a patient. Thus, the hemodynamic demand of the patient is met. Sensor means for determining the hemodynamic demand of a patient allow for rate adaptive pacing wherein the controlled stimulation rate is determined based on the hemodynamic demand of the patient as determined by the sensor means and the controlled stimulation rate is adapted accordingly. A strong hemodynamic demand leads to a high controlled stimulation rate.

Further, the controlled stimulation rate of ventricular stimulation pulses may depend on a rate of sensed intrinsic atrial contraction when atrial synchronous pacing is performed where no natural (intrinsic) ventricular contraction can be sensed within a predetermined atrioventricular interval (AVD) after a sensed atrial contraction. In such case, a high atrial rate leads to a high controlled ventricular stimulation rate.

If the heart stimulator is designed as an implantable cardioverter/defibrillator, a high controlled stimulation rate may be triggered in order to treat or prevent tachycardia or fibrillation of a heart chamber.

In order to monitor the heart chamber and thus to determine whether or not a contraction of a heart chamber has occurred a pacemaker has a sensing stage for sensing a heart parameter indicating a natural (intrinsic) or stimulated contraction of a heart chamber.

The sensing stage can be connected to an electrode placed in a respective heart chamber. A contraction of a heart chamber can be detected by evaluating electrical potentials sensed by such sensing electrode.

Alternatively, the sensing stage can be designed to response to the mechanical action of the heart. One way of detecting mechanical action of the heart is to evaluate an time course of intracardiac impedance.

Providing a sensing stage for a heart chamber to be stimulated allows for inhibition of delivery of a stimulation pulse to that chamber in case an intrinsic contraction of said chamber occurs within a respective atrial or ventricular escape interval. Such mode of pacing or stimulating a heart is called demand mode because a heart chamber only is stimulated if there is a demand whereas a stimulation pulse is skipped (inhibited) if there is no demand because the heart chamber has contracted on it's own.

Many heart stimulators are capable to perform a number of different stimulation that are characterized by a commonly known three letter code wherein the first letter designates the chamber or chamber to be stimulated like V for a ventricle to be stimulated, A for an atrium to be stimulated and D (dual) for both, ventricle and atrium to be stimulated. Similarly, the second letter characterizes the chamber or chambers the heart stimulator can pick up sensed signals from (V: ventricle, A: atrium, D: ventricle and atrium). The third letter characterizes the mode of delivery of stimulation pulses: T=triggered, I=inhibited and D=dual (T+I). A fourth letter "R" may characterize a rate adaptive heart stimulator.

Regarding application of a high controlled stimulation rate to a heart chamber, it is to be noticed that a fault in a cardiac pacemaker causing a sustained high pacing rate could lead to driving a patient's heart to a state where an ischemia develops, leading to harmful tachycardia.

In order to avoid such consequences of a pacemaker's fault cardiac pacemakers usually comprise a separate circuit with an independent oscillator for monitoring the stimulation rate and to inhibit stimulation pulses that could exceed a give rate threshold. This feature often times is called runaway protection. Pacemakers provide for features that include legitimate conditions in which temporarily violating such rate limit said by the runaway protection is necessary. For example, the delivery of a backup stimulation pulse after a non-effective stimulation pulse should occur with a rate that is higher than a certain rate limit. Another example of a feature where a higher stimulation rate is required is the delivery of a burst of stimulation pulses intended to trigger or to stop arrhythmias. In order to allow for such features, prior art pacemakers comprise means to temporarily disable or override the runaway protection. In order to reduce the probability of inadvertently activating the means for overriding the runaway protection, these overriding means are usually designed with a certain degree of intentional complexity.

It is an object of the present invention to provide a heart stimulator with improved means for runaway protection.

SUMMARY OF THE INVENTION

According to the present invention the object of the invention is achieved by a heart stimulator featuring at least one sensing stage connected or being connectable to an electrode lead comprising an electrode for picking up electric potentials inside a heart chamber, said sensing stage being adapted to sense an excitation of a heart chamber by way of picked up electric potentials, at least one stimulation pulse generator adapted to generate electric stimulation pulses and being connected or being connectable to an electrode lead comprising a stimulation electrode for delivering electric stimulation pulses to said chamber of a heart, a control unit being connected to said sensing stage and to said stimulation pulse generator and being adapted to trigger stimulation pulses to be generated by the stimulation pulse generator and to be delivered via said electrode lead, said stimulation pulses being triggered with a controlled stimulation rate controlled by the control unit, and a rate monitoring stage and being connected to the control unit and being adapted to monitor an average of said controlled stimulation rate over a predetermined time window and override the controlled stimulation rate by a fixed stimulation rate for a predetermined period of time if the average controlled stimulation rate exceeds a predetermined maximum rate.

The rate monitoring stage according to the claimed invention does not generally limit the control stimulation rate but rather simply monitors said control stimulation rate and only occasionally triggers a fixed stimulation rate for a predetermined period of time.

Preferably, the rate monitoring stage comprises or is connected to an independent oscillator that is independent from an oscillator providing a clock signal to the control unit for timing the controlled stimulation pulses. Furthermore, a rate monitoring state preferably forms a separate circuit that is separate from the circuit forming the control unit.

In a preferred embodiment, the rate monitoring stage is adapted to trigger the fixed stimulation rate if the average control stimulation rate exceeds the predetermined maximum rate within a time window of two minutes.

A preferred maximum for the average of the control stimulation rate in said predetermined time window is 180 pulses per minute (ppm). Thus, if the rate monitoring stage monitors an average controlled stimulation rate over a time window of preferably two minutes that exceeds 180 ppm, the rate monitoring stage triggers stimulation with the fixed stimulation rate.

Preferably, the fixed stimulation rate is a medium stimulation rate between 60 and 100 ppm.

Further, the fixed stimulation rate preferably is delivered in a VVI-mode of pacing where only the ventricle is stimulated in a demand mode of pacing.

If all preferred features are equally realized, the heart stimulator provides for a separate circuit forming a rate monitoring stage with an independent oscillator to monitor the average stimulation rate within a proceeding time window of i.e. two minutes. If this average stimulation rate thus determined exceeds an average maximum rate expected to be occasionally tolerable (i.e. a continuous stimulation rate of 180 ppm, combined with an antitachycardia pacing burst episode), the separate circuit (rate monitoring stage) overrides the controlled stimulation rate with a fixed stimulation rate for a predetermined period of time of e. g. five minutes, which is long enough to allow the heart to recover sufficiently from the induced ischemia to greatly reduce the probability of induction of a harmful tachyarrhythmia. The fixed stimulation rate is delivered in a VVI mode of pacing requiring that the separate (independent) circuit for controlling the delivery of stimulation pulses with said fixed stimulation rate has access to at least ventricular sense information. In said VVI mode, no atrial stimulation pulses are delivered nor are atrial sense signals evaluated.

Allowing short periods of pacing above an average of e.g. 180 ppm, interleaved with longer periods of limited rate pacing should allow the heart to recover from the cumulative effects of being driven to its maximum rate sufficiently to avoid induction of harmful tachyarrhythmia in most cases. This will greatly reduce the probability of death due to a runaway stimulation fault.

BRIEF DESCRIPTION OF THE DRAWINGS

The above and other aspects, features and advantages of the present invention will be more apparent from the following more particular description thereof, presented in conjunction with the following drawings wherein.

DETAILED DESCRIPTION OF THE INVENTION

The following description is of the best mode presently contemplated for carrying out the invention. This description is not to be taken in a limiting sense, but is made merely for the purpose of describing the general principles of the invention. The scope of the invention should be determined with reference to the claims.

Figure 1:
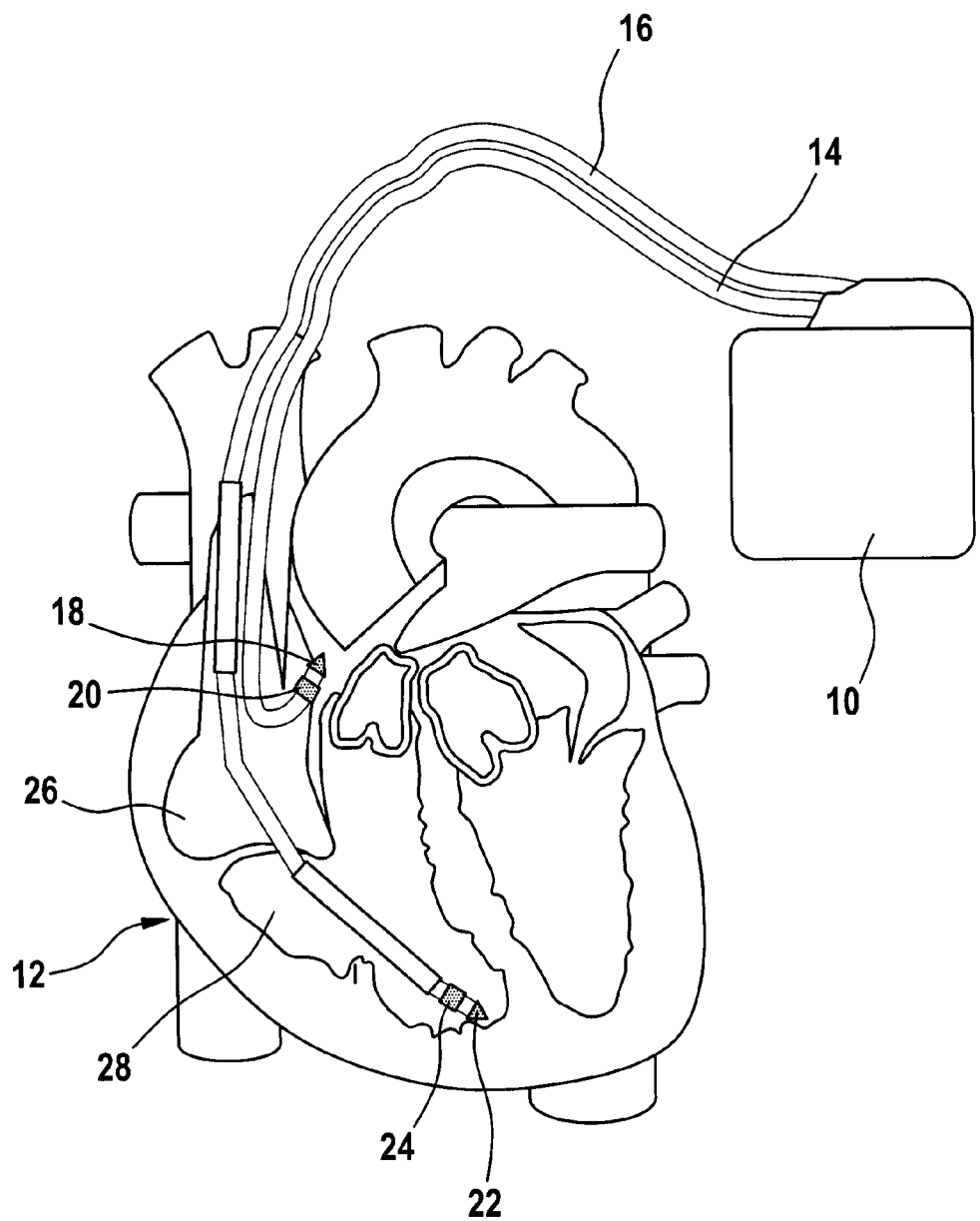
FIG. 1 shows a dual chamber pacemaker being a heart stimulator connected to leads placed in a heart.

FIG. 1 shows a dual chamber pacemaker 10 as heart stimulator connected to pacing/sensing leads placed in a heart 12 is illustrated. The pacemaker 10 is coupled to a heart 12 by way of leads 14 and 16. Lead 14 has a pair of right atrial electrodes 18 and 20 that are in contact with the right atria 26 of the heart 12. Lead 16 has a pair of electrodes 22 and 24 that are in contact with the right ventricle 28 of heart 12. Electrodes 18 and 22 are tip-electrodes at the very distal end of leads 14 and 15, respectively. Electrode 18 is a right atrial tip electrode RA-Tip and electrode 22 is a right ventricular tip electrode 22. Electrodes 20 and 24 are ring electrodes in close proximity but electrically isolated from the respective tip electrodes 18 and 22. Electrode 20 forms a right atrial ring electrode RA-Ring and electrode 24 forms a right ventricular ring electrode RV-Ring.

Figure 2:
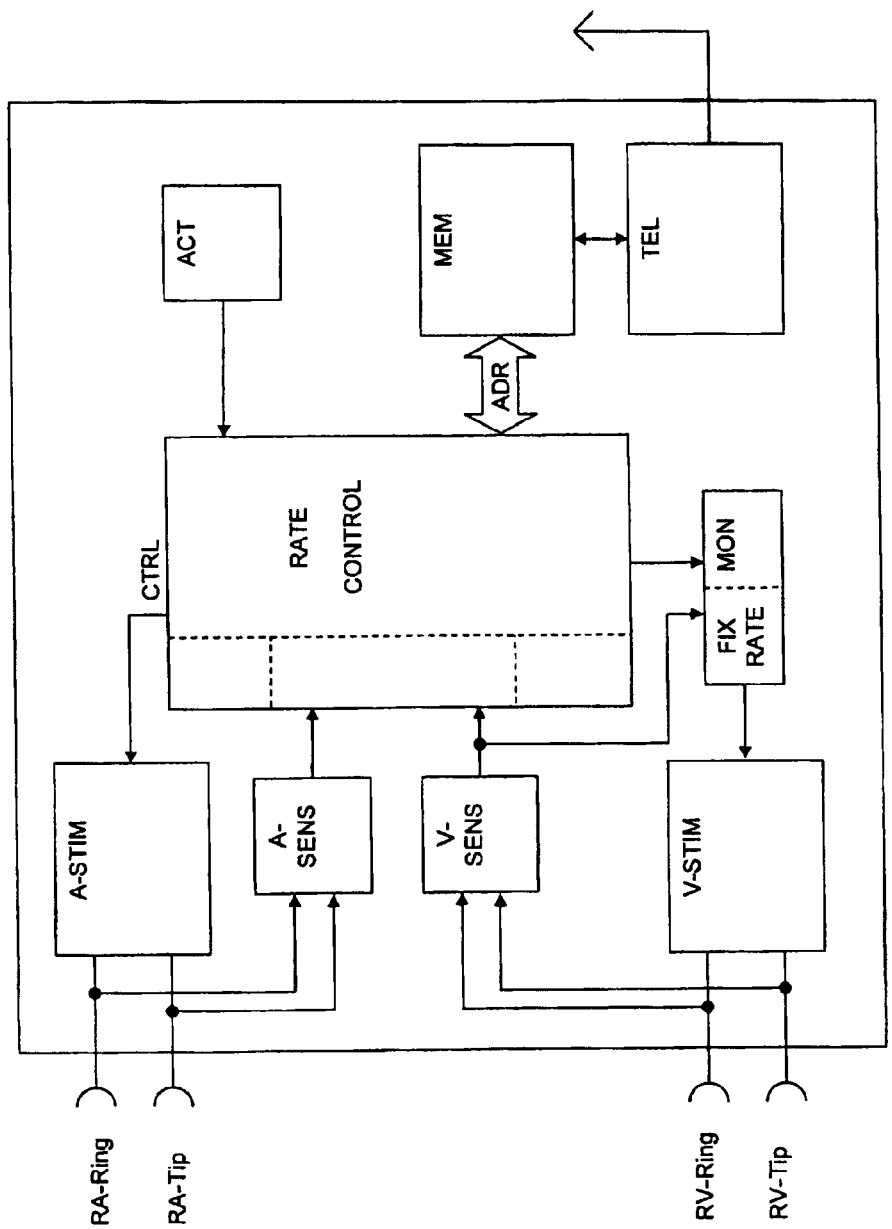
FIG. 2 shows a block diagram of a heart stimulator according to the invention.

Referring to FIG. 2 a simplified block diagram of a dual chamber pacemaker 10 is illustrated. During operation of the pacemaker leads 14 and 16 are connected to respective output/input terminals of pacemaker 10 as indicated in FIG. 1 and carry stimulating pulses to the tip electrodes 18 and 22 from an atrial stimulation pulse generator A-STIM and a ventricular pulse generator V-STIM, respectively. Further, electrical signals from the atria are carried from the electrode pair 18 and 20, through the lead 14, to the input terminal of an atrial channel sense amplifier A-SENSE; and electrical signals from the ventricles are carried from the electrode pair 22 and 24, through the lead 16, to the input terminal of a ventricular sense channel amplifier R-SENSE.

Controlling the dual chamber pacer 10 is a control unit CTRL that is connected to sense amplifiers A-SENSE and V-SENSE and to stimulation pulse generators A-STIM and V-STIM. Control unit CTRL receives the output signals from the atrial sense amplifier A-SENSE and from the ventricular sense amplifier V-SENSE. The output signals of sense amplifiers A-SENSE and V-SENSE are generated each time that a P-wave or an R-wave, respectively, is sensed within the heart 12.

Control unit CTRL also generates trigger signals that are sent to the atrial stimulation pulse generator A-STIM and the ventricular stimulation pulse generator V-STIM, respectively. These trigger signals are generated each time that a stimulation pulse is to be generated by the respective pulse generator A-STIM or V-STIM. The atrial trigger signal is referred to simply as the "A-pulse", and the ventricular trigger signal is referred to as the "V-pulse". During the time that either an A-pulse or V-pulse is being delivered to the heart, the corresponding sense amplifier, A-SENSE and/or R-SENSE, is typically disabled by way of a blanking signal presented to these amplifiers from the control unit CTRL, respectively. This blanking action prevents the sense amplifiers A-SENSE and V-SENSE from becoming saturated from the relatively large stimulation pulses that are present at their input terminals during this time. This blanking action also helps prevent residual electrical signals present in the muscle tissue as a result of the pacer stimulation from being interpreted as P-waves or R-waves.

Control unit CTRL comprises circuitry for timing ventricular and/or atrial stimulation pulses according to an adequate stimulation rate that can be adapted to a patient's hemodynamic need as pointed out below. The circuitry for timing ventricular and/or atrial stimulation pulses comprises an oscillator (not shown) generating a clock signal for the control unit. The control unit's oscillator either is part of said circuitry for timing ventricular and/or atrial stimulation pulses or is connected to said circuitry.

Still referring to FIG. 2, the pacer 10 may also include a memory circuit MEM that is coupled to the control unit CTRL over a suitable data/address bus ADR. This memory circuit MEM allows certain control parameters, used by the control unit CTRL in controlling the operation of the pacemaker 10, to be programmably stored and modified, as required, in order to customize the pacemaker's operation to suit the needs of a particular patient. Such data includes the basic timing intervals used during operation of the pacemaker. Further, data sensed during the operation of the pacer may be stored in the memory MEM for later retrieval and analysis.

A telemetry circuit TEL is further included in the pacemaker 10. This telemetry circuit TEL is connected to the control unit CTRL by way of a suitable command/data bus. Telemetry circuit TEL allows for wireless data exchange between the pacemaker 10 and some remote programming or analyzing device which can be part of a centralized service center serving multiple pacemakers.

The pacemaker 10 in FIG. 1 is referred to as a dual chamber pacemaker because it interfaces with both the right atrium 26 and the right ventricle 28 of the heart 10. Those portions of the pacemaker 10 that interface with the right atrium, e.g., the lead 14, the P-wave sense amplifier A-SENSE, the atrial stimulation pulse generator A-STIM and corresponding portions of the control unit CTRL, are commonly referred to as the atrial channel. Similarly, those portions of the pacemaker 10 that interface with the right ventricle 28, e.g., the lead 16, the R-wave sense amplifier V-SENSE, the ventricular stimulation pulse generator V-STIM, and corresponding portions of the control unit CTRL, are commonly referred to as the ventricular channel.

In order to allow rate adaptive pacing in a DDDR mode, the pacemaker 10 further includes a physiological sensor ACT that is connected to the control unit CTRL of the pacemaker 10. While this sensor ACT is illustrated in FIG. 2 as being included within the pacemaker 10, it is to be understood that the sensor may also be external to the pacemaker 10, yet still be implanted within or carried by the patient. A common type of sensor is an activity sensor, such as a piezoelectric crystal, mounted to the case of the pacemaker. Other types of physiologic sensors are also known, such as sensors that sense the oxygen content of blood, respiration rate, pH of blood, body motion, and the like. The type of sensor used is not critical to the present invention. Any sensor capable of sensing some physiological parameter relatable to the rate at which the heart should be beating can be used. Such sensors are commonly used with "rate-responsive" pacemakers in order to adjust the rate of the pacemaker in a manner that tracks the physiological needs of the patient.

As is apparent from FIG. 2, a separate rate monitoring stage FIX RATE/MON formed by a separate circuit is provided for monitoring the ventricular stimulation rate as controlled by the control unit CTRL and occasionally override the controlled variable stimulation rate by a fixed stimulation rate. The rate monitoring stage is connected to the control unit CTRL and to the ventricular sensing stage V-SENSE and the ventricular stimulation stage V-STIM.

The rate monitoring stage continuously monitors the average ventricular stimulation rate as controlled by the control unit by way of a proceeding time window of 2 minutes duration. If the average of the controlled stimulation rate exceeds 180 pulses per minute (ppm) the rate monitoring stage FIX RATE/MON overrides the controlled stimulation rate as controlled by the control unit CTRL by a fixed stimulation rate of, e.g. 80 ppm for a predetermined period of time of 5 minutes. Stimulation of the ventricle during said predetermined period of time is performed in a VVI mode of pacing wherein stimulation pulses are only delivered to the ventricle if no intrinsic ventricular is sensed during a ventricular escape interval.

The concept of permanently monitoring the controlled stimulation rate and interrupting high rate stimulation with an average stimulation rate over 180 ppm after two minutes by moderate rate stimulation for e.g. 5 minutes guaranties that the heart always can sufficiently recover from high rate pacing thus avoiding an ischemia.

In order to allow for determination of the average stimulation rate independently from the control unit's circuitry's clock generator, the rate monitoring stage features a separate rate monitor's oscillator for generating a clock signal for the rate monitoring stage. The rate monitor's oscillator either as an integral part of the separate circuit forming the rate monitoring stage or as a clock generator being connected to the rate monitoring stage.

Although an exemplary embodiment of the present invention has been shown and described, it should be apparent to those of ordinary skill that a number of changes and modifications to the invention may be made without departing from the spirit and scope of the invention.

For example, the concept of sustained high rate protection can be applied to one, two, three or four chamber pacemakers without departing from the claimed invention. This invention can readily be adapted to such devices by following the present teachings. All such changes, modifications and alterations should therefore be recognized as falling within the scope of the present invention.

What is claimed is:

1. A heart stimulator for stimulating a chamber of a heart by way of electrical stimulation pulses, said simulator comprising:
    a sensing stage connected or being connectable to an electrode lead comprising an electrode for picking up electric potentials inside a heart chamber, said sensing stage being adapted to sense an excitation of a heart chamber by way of picked up electric potentials,
    a stimulation pulse generator adapted to generate electric stimulation pulses and being connected or being connectable to an electrode lead comprising a stimulation electrode for delivering electric stimulation pulses to said chamber of a heart,
    a control unit being connected to said sensing stage and to said stimulation pulse generator and being adapted to trigger stimulation pulses to be generated by the stimulation pulse generator and to be delivered via said electrode lead, said stimulation pulses being triggered with a controlled stimulation rate controlled by the control unit, and a monitoring stage and being connected to the control unit and being adapted to monitor said controlled stimulation rate and override the controlled stimulation rate by a fixed stimulation rate for a preset and fixed period of time if the controlled stimulation rate exceeds a predetermined maximum rate.

2. The heart stimulator according to claim 1 wherein the control unit comprises or is connected to an oscillator generating a clock signal for the control unit and wherein the monitoring unit comprises or is connected to a separate oscillator for determining the average controlled stimulation rate independently from the control unit's oscillator.

3. The heart stimulator according to claim 2 wherein the monitoring stage is formed by a separate circuit that is separate from a circuit comprising the control unit.

4. The heart stimulator according to claim 1 wherein the monitoring stage is adapted to determine an average of the controlled stimulation rate over a preset and fixed averaging time window and to override the controlled stimulation rate by the fixed stimulation rate if the average of the controlled stimulation rate exceeds the predetermined maximum rate.

5. The heart stimulator according to claim 4 wherein the time window for determining the average controlled stimulation rate is a preceding averaging time window that has a duration between 1 and 3 minutes.

6. The heart stimulator according to claim 1 wherein the preset and fixed period of time of delivering stimulation pulses with a fixed stimulation rate has a duration between 2 and 10 minutes.

7. The heart stimulator according to claim 1 wherein the monitoring stage is adapted to trigger stimulation pulses to a ventricle of a heart with a fixed stimulation rate in a VVI stimulation mode during said preset and fixed period of time.

8. A heart stimulator for stimulating a heart with electrical stimulation pulses, the stimulator including:
   a. a sensing stage:
      (1) being connected or being connectable to a sensing electrode lead which picks up electric potentials from a heart,
      (2) sensing excitation of the heart via the picked up electric potentials;
   b. a stimulation pulse generator:
      (1) generating electric stimulation pulses, and
      (2) being connected or being connectable to a stimulating electrode lead which
         delivers the generated electric stimulation pulses to the heart,
   c. a control unit triggering the stimulation pulses to be generated by the stimulation pulse generator and to be delivered via the stimulating electrode lead, the stimulation pulses being triggered at a controlled stimulation rate, wherein the controlled stimulation rate is changed to a different and fixed stimulation rate for a preset and fixed period of time if the average of the controlled stimulation rate over a preset and fixed averaging time window exceeds a predetermined maximum rate.

9. The heart stimulator of claim 8 wherein the preset and fixed averaging time window for determining the average of the controlled stimulation rate has a duration of 1-3 minutes.

10. The heart stimulator of claim 9 wherein the preset and fixed period of time of delivering the stimulation pulses at the different and fixed stimulation rate has a duration between 2 and 10 minutes.

11. The heart stimulator of claim 8 wherein the preset and fixed period of time of delivering the stimulation pulses at the different and fixed stimulation rate has a duration between 2 and 10 minutes.

12. The heart stimulator of claim 11 wherein the preset and fixed averaging time window for determining the average of the controlled stimulation rate has a duration of greater than one minute.

13. A heart stimulator for stimulating a heart with electrical stimulation pulses, the stimulator including:
   a. a sensing stage obtaining electric potentials from a heart chamber,
   b. a stimulation pulse generator generating electric stimulation pulses for delivery to the heart chamber at a stimulation rate;
   c. a control unit setting the stimulation rate, wherein:
      (1) the stimulation rate is ordinarily a controlled rate, and
      (2) the stimulation rate is temporarily changed to a fixed stimulation rate:
         (a) different from the controlled rate, and
         (b) for a preset and fixed period of time.
         if the average of the stimulation rate over a preset and fixed averaging time window exceeds a predetermined maximum rate.

14. The heart stimulator of claim 13 wherein the preset and fixed period of time for delivering the stimulation pulses at the fixed stimulation rate is between approximately 2 and 10 minutes.

15. The heart stimulator of claim 14 wherein the preset and fixed averaging time window for determining the average of the stimulation rate is between approximately 1 and 3 minutes.

* * * * *